Figure 1:
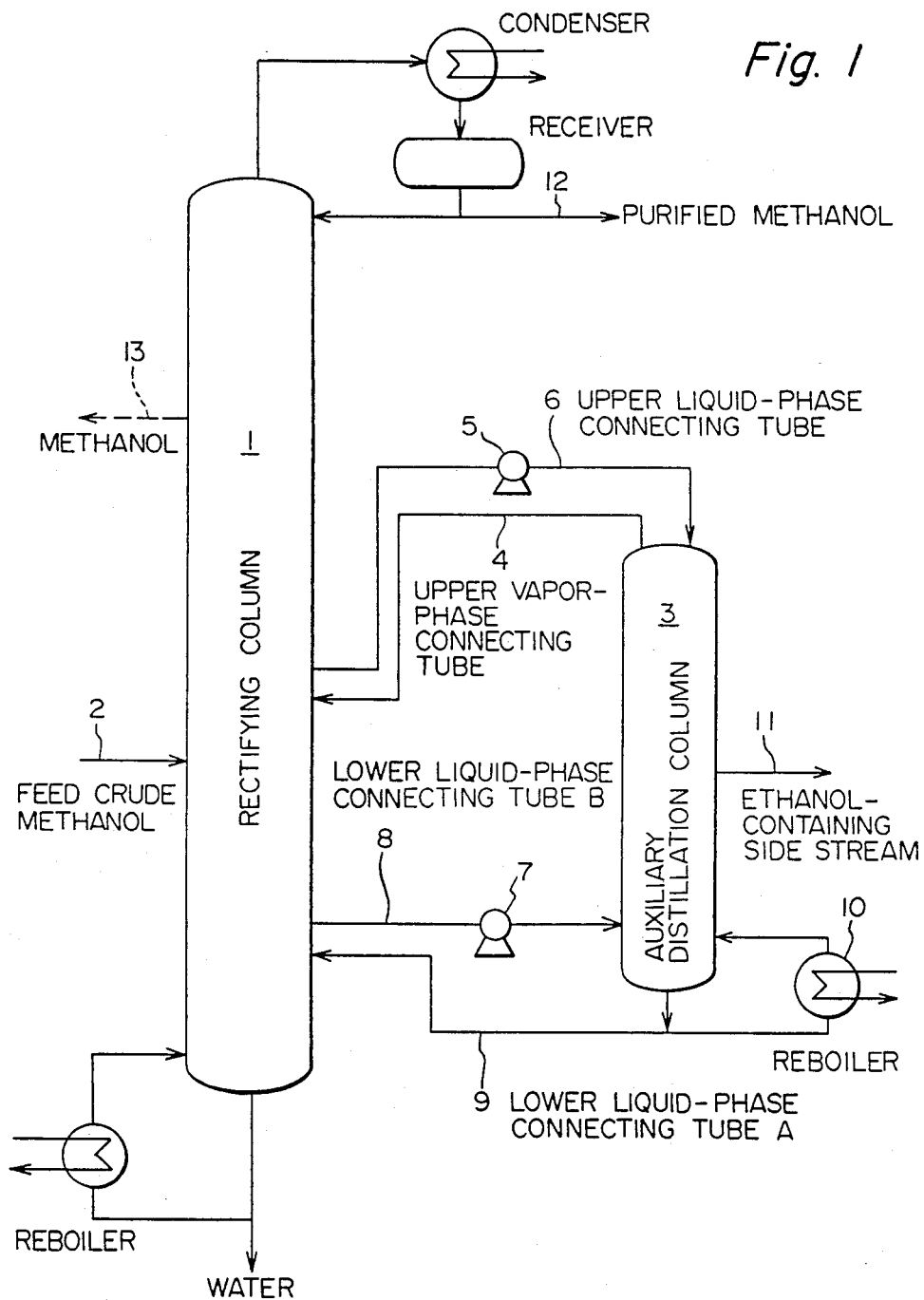

United States Patent [19]

Saito et al.

[11] Patent Number: 4,744,869

[45] Date of Patent: May 17, 1988

[54] PROCESS FOR PURIFYING METHANOL

[75] Inventors: Yoshihiko Saito; Osamu Hashimoto, both of Niigata, Japan

[73] Assignee: Mitsubishi Gas Chemical Company, Inc., Tokyo, Japan

[21] Appl. No.: 897,371

[22] Filed: Aug. 18, 1986

[30] Foreign Application Priority Data

Aug. 16, 1985 [JP] Japan .................. 60-180168

[51] Int. Cl.$^4$ ............................. B01D 3/34
[52] U.S. Cl. ...................... 203/82; 203/83; 203/84; 203/85; 203/99; 203/DIG. 13; 203/DIG. 19; 203/DIG. 23; 568/913
[58] Field of Search ................. 203/81–85, 203/99, DIG. 19, DIG. 23, DIG. 13; 568/913; 261/151

[56] References Cited

U.S. PATENT DOCUMENTS

| | | | |
|---|---|---|---|
| 2,549,290 | 4/1951 | Congdon et al. | 203/DIG. 23 |
| 2,595,805 | 5/1952 | Morrell et al. | 203/82 |
| 3,239,435 | 3/1966 | Conseiller et al. | 203/DIG. 23 |
| 3,406,100 | 10/1968 | Karafian | 203/78 |
| 3,434,937 | 3/1969 | Elliot et al. | 203/DIG. 23 |
| 3,445,345 | 5/1969 | Katzen et al. | 203/99 |
| 4,013,521 | 3/1977 | Scott | 203/DIG. 19 |
| 4,149,940 | 4/1979 | Pinto | 203/DIG. 19 |
| 4,210,495 | 7/1980 | Pinto | 203/DIG. 19 |
| 4,246,073 | 1/1981 | Umeda et al. | 203/25 |

FOREIGN PATENT DOCUMENTS

| | | |
|---|---|---|
| 0132268 | 9/1978 | Fed. Rep. of Germany ... 203/DIG. 19 |
| 2856051 | 7/1979 | Fed. Rep. of Germany ... 203/DIG. 19 |
| 42-2046 | 1/1967 | Japan . |

OTHER PUBLICATIONS

Hirata et al., "Energy-Saving Distillation Technique", Chemical Engineering, vol. 41, No. 9, pp. 454–477 (1977).

Primary Examiner—S. Leon Bashore
Assistant Examiner—V. Manoharan
Attorney, Agent, or Firm—Wenderoth, Lind & Ponack

[57] ABSTRACT

A process for purifying methanol which comprises introducing crude synthetic methanol obtained by catalytic reaction of carbon oxide and hydrogen into a rectifying column either as such or after it is first introduced into a topping column and distilled with or without the addition of water to remove low-boiling components from the top of the topping column, and distilling it in the rectifying column to withdraw purified methanol from the top of the column and mainly water from the bottom of the column; wherein an auxiliary distillation column is provided side by side with the rectifying column, and the rectifying column and the auxiliary distillation column are operated under particular conditions.

9 Claims, 2 Drawing Sheets

PROCESS FOR PURIFYING METHANOL

This invention relates to a process for purifying methanol, and more specifically, to a process for producing a novel and improved purification process for obtaining highly pure methanol containing very small amounts of impurities such as ethanol from crude synthetic methanol prepared by the catalytic reaction of carbon oxide and hydrogen.

Crude methanol synthesized by reacting carbon oxide with hydrogen in the presence of a catalyst under pressure usually contains many impurities such as water, higher alcohols (ethanol, butanol, etc.), paraffins, ketones, ethers, and esters. A general method of removing these impurities from the crude methanol comprises introducing the crude methanol into a topping column, distilling it, optionally after the addition of water, to remove low-boiling impurities such as ketones, ethers and paraffins as an overhead fraction, introducing the water-containing methanol into a rectifying column, and further distilling it to separate purified methanol from the top of the column and water from the bottom of the column. However, when methanol is purified by this method, higher alcohols such as ethanol build up in the middle of the rectifying column. It was proposed to reduce the amount of ethanol by withdrawing a liquid phase or a gaseous phase as a side stream from the middle of the rectifying column (U.S. Pat. No. 3,406,100, and Japanese Patent Publication No. 2046/1967). In recent years, the requirement in regard to the ethanol content of purified methanol has become increasingly rigorous, and for example, in certain applications, methanol having an ethanol content of less than 10 ppm is required. This rigorous requirement cannot be met by the above-cited methods previously proposed.

As a general means of saving energy in a distillation process, it is known to introduce a liquid feed to be introduced into a rectifying column into an auxiliary distillation column having a lesser number of plates, and to provide tubes at the top and bottom of the distillation column which lead to the rectifying column [M. Hirata et al., "Energy-Saving Distillation Technique", Chemical Engineering, vol. 41, No. 9, pages 454–477 (1977)]. This distillation process is known as the Petlyuk-type distillation method. When this method is applied to the distillation of crude methanol, the distribution of the vapor to the auxiliary distillation column from the rectifying column is small, and the distillation is difficult to carry out satisfactorily.

It is an object of this invention to provide an improved process for rectifying methanol, which eliminates the defects of the Petlyuk-type distillation process as applied to the purification of crude methanol, and which can effect more efficient removal of ethanol from methanol in a rectifying column while achieving energy saving, and which is easy to operate.

According to this invention, there is provided a process for purifying methanol which comprises introducing crude synthetic methanol obtained by catalytic reaction of carbon oxide and hydrogen into a rectifying column either as such or after it is first introduced into a topping column and distilled with or without the addition of water to remove low-boiling components from the top of the initial distillation column, and distilling it in the rectifying column to withdraw purified methanol from the top of the column and mainly water from the bottom of the column; wherein (A) an auxiliary distillation column is provided side by side with the rectifying column,
 (a) a vapor-phase portion on a plate at the top of the auxiliary distillation column is connected to a vapor-phase portion on a plate slightly above a material feed plate of the rectifying column by means of an upper vapor-phase connecting tube,
 (b) a liquid-phase portion on a plate at the top of the auxiliary distillation column is connected to a liquid-phase portion on said plate slightly above the material feed plate of the rectifying column by means of an upper liquid-phase connecting tube via a pump,
 (c) a liquid-phase portion on a plate at the bottom of the auxiliary distillation column is connected to a liquid-phase portion on a plate located between said bottom plate and a material feed plate of the rectifying column directly or via a pump by means of a lower liquid-phase connecting tube A, and
 (d) a liquid-phase portion on a plate near the bottom of the auxiliary distillation column is connected to a liquid-phase portion on a plate located between the bottom plate and the material feed plate of the rectifying column via a pump by means of a lower liquid-phase connecting tube B, (B) a reboiler is provided at the bottom portion of the auxiliary distillation column and by heating the reboiler, the bottom components of the auxiliary distillation column are evaporated, (C) the vapor components are conducted from the top of the auxiliary distillation column to the rectifying column by the upper vapor phase connecting tube, (D) the liquid components are forcibly conducted from the rectifying column to the top of the auxiliary distillation column via a pump by means of the upper liquid-phased connecting tube, (E) the liquid components are conducted from the bottom of the auxiliary distillation column to the lower portion of the rectifying column directly or via a pump by means of the lower liquid-phase connecting tube A, (F) the liquid components are forcibly conducted from the lower portion of the rectifying column to the bottom of the auxiliary distillation column via a pump by means of the lower liquid-phase connecting tube B, (G) thereby the distillation is carried out while circulating the vapor components and the liquid components between the rectifying column and the auxiliary distillation column, and (H) purified methanol is withdrawn from the top of the rectifying column, and a side stream rich in ethanol is withdrawn from the liquid-phase portion of a plate located in the middle part of the auxiliary distillation column.

One characteristic feature of the process for purifying crude methanol in accordance with this invention is that the auxiliary distillation column is provided side by side with the rectifying column, and the distillation is carried out while circulating the vapor and liquid components between the rectifying column and the auxiliary distillation column.

The auxiliary distillation column disposed side by side with the rectifying column in this invention needs not be of any particular structure, and may be an ordinary distillation column such as a tray column or a packed column. The size of the auxiliary distillation column depends upon the size of the rectifying column used, and generally it has a smaller diameter and less distillation plates than the rectifying column. Specifically, the number of plates of the auxiliary distillation column may generally be from 1/5 to 4/5, preferably from 1/3 to 2/3, of the number of plates of the rectifying column, and distillation columns having a theoretical plate number of about 10 to about 40, preferably about 17 to about 33 can be advantageously used.

On the other hand, the rectifying column may be any of those which are normally used in the purification of crude methanol, i.e. tray column such as bubble caps and sieve trays, or packed columns.

According to the process of this invention, a vapor-phase portion on a plate at the top of the auxiliary distillation column is connected to a vapor-phase portion on a plate slightly above a material feed plate of the rectifying column by an upper vapor-phase connecting tube. The term "plate slightly above the material feed plate", as used herein, means a plate positioned within the range from the first to about the 20th plate above the material feed plate of the rectifying column. Generally, the starting material is frequently fed to a plate located at a position within the range of from 12/20 to 17/20 of the number of plates of the rectifying column counted from its top. For example, if the material is fed to a position 17/20 of the number of plate counted from the top of the column, the upper vapor-phase connecting tube can be connected to the vapor-phase portion on a plate located at a position, for example, within the range of from 9/20 to 17/20, preferably from 13/20 to 16/20, of the number of plates of the rectifying column counted from its top.

The number of plates of the rectifying column and the auxiliary distillation column is the number of theoretical plates unless otherwise stated.

The liquid-phase portion on a plate at the top of the auxiliary distillation column is connected to the liquid-phase portion on the aforesaid plate slightly above the rectifying column, namely that plate of the rectifying column to which the aforesaid upper vapor-phase connecting tube is connected. The pump operates so as to conduct the liquid-phase components of the above plate of the rectifying column to the auxiliary distillation column. At this time, the amount of the liquid-phase components flowing from the rectifying column to the auxiliary distillation column is suitably adjusted generally to 0.3 to 0.6 times, preferably 0.4 to 0.5 times, the amount of the liquid-phase descending through the rectifying column. The term "amount of the liquid-phase descending through the rectifying column", as used herein, means the amount of the liquid phase which descends from the top of the rectifying column to that plate to which the upper liquid-phase connecting tube is connected.

On the other hand, the liquid-phase portion on a plate at the bottom of the auxiliary distillation column is connected to the liquid-phase portion on any plate positioned between the material feed plate and the bottom plate of the rectifying column by a first lower liquid-phase connecting tube A either forcibly via a pump or directly without the intermediary of a pump, and the liquid components are circulated from the liquid-phase portion of the bottom of the auxiliary distillation column is circulated to the rectifying column. The connecting site of the lower liquid-phase connecting tube A to the rectifying column is not strictly restricted if it is between the material feed plate and the bottom plate. Generally, it is conveniently connected to the liquid-phase portion of a plate located within the range of from 1/40 to 3/20, preferably from 1/40 to 1/10, of the number of plates of the rectifying column counted from its bottom.

The amount of the bottom liquid-phase components of the auxiliary distillation column circulated to the rectifying column from the bottom of the auxiliary distillation column may usually be 1/2 to 2 times the amount of the liquid phase fed from the rectifying column to the auxiliary distillation column via the upper liquid-phase connecting tube.

A liquid-phase portion on a plate near the bottom of the auxiliary distillation column is connected to a liquid-phase portion on a plate positioned between the material feed plate and the bottom plate of the rectifying column via a pump by means of a second lower liquid-phase connecting tube B, and the liquid-phase components of the aforesaid plate of the rectifying column are circulated to a site near the bottom of the auxiliary distillation column. The term "plate near the bottom of the auxiliary distillation column" denotes that plate which is at the bottom of the auxiliary distillation column or up to about 5 plates above the bottom.

That site of the rectifying column to which the second lower liquid-phase connecting tube B is connected is not strictly restricted if it is between the material feed plate and the bottom plate. Generally, it is desirably connected to the liquid-phase portion on a plate positioned within the range of from 1/40 to 3/20, preferably from 1/40 to 1/10, of the number of plates of the rectifying column, especially desirably to the same plate as that to which the lower liquid-phase connecting tube A is connected or any plate up to about 5 plates above it.

When a reboiler provided at the bottom of the auxiliary distillation column is heated, the bottom components of the auxiliary distillation column are evaporated to effect distillation. The operating conditions for the auxiliary distillation column vary depending upon the kinds and amounts of impurities in the starting material fed to the rectifying column, the operating conditions for the rectifying column, etc. Generally, the auxiliary distillation column is operated at a pressure equal to, or slightly higher than, the pressure at which the rectifying column is operated.

On the other hand, the rectifying column may be operated as in the conventional rectification of crude synthetic methanol. Generally, the rectifying column is operated under atmospheric pressure or a slightly elevated pressure at a reflux ratio of from 0.8 to 3, preferably from 1 to 2.

Vapor-phase and liquid-phase components are forcibly circulated between the rectifying column and the auxiliary distillation column disposed side by side when reboilers provided at the bottom portions of these columns are heated and the pumps provided at the upper liquid-phase connecting tube and the lower liquid-phase connecting tube B are set in operation. Consequently, the vapor-phase components can be surely distributed from the rectifying column to the auxiliary distillation column. Specifically, according to the process of this invention, the intermediate portion of the rectifying column excepting the vicinity of the top and the bottom assumes a double structure, and distillation is carried out with heat exchange between the liquid and vapor phases. During this time, ethanol in the crude methanol is concentrated near the middle of the auxiliary distillation column. By withdrawing ethanol as a side stream out of the auxiliary distillation column, ethanol can be separated and removed efficiently from the crude methanol, and highly purified methanol can be recovered from the top of the rectifying column.

Crude synthetic methanol which can be purified by the process of this invention is obtained by catalytically reacting carbon oxide (carbon monoxide or carbon dioxide) with hydrogen. This catalytic reaction can be carried out by a methods known per se, for example the method described in U.S. Pat. No. 3,971,735. Examples of the catalyst used in this reaction include a copper-zinc type catalyst, a copper-zinc-aluminum type catalyst, a copper-zinc-boron type catalyst, a copper-zinc-aluminum-boron type catalyst, a copper-zinc-chromium type catalyst, a copper-zinc-silica type catalyst and a copper-zinc-phosphate catalyst. The reaction temperature is generally 160° to 300° C., preferably 200° to 280° C., and the reaction pressure is generally 40 to 150 atmosphere, preferably 60 to 110 atmospheres. Under these conditions, the reactor can be operated by passing carbon oxide and hydrogen usually in a mole ratio of from 1:2 to 1:3 through a catalyst bed at a space velocity of 4,000 to 40,000 $hr^{-1}$, preferably 6,000 to 20,000 $hr^{-1}$.

Crude methanol obtained by the above catalytic reaction can be directly fed as a starting material into the rectifying column. Alternatively, it may be first conducted to a topping column and distilled with or without water and after distilling off low-boiling components from the top of the column, the residue may then be fed to the rectifying column.

Pre-distillation of crude synthetic methanol in the topping column may be carried out under atmospheric pressure or a slightly elevated pressure utilizing a heat source of a relatively low level of temperature of about 90° C.

According to the process of this invention described above, highly pure methanol is obtained from the top of the rectifying column, and mainly water is withdrawn from the bottom of the column.

According to the process of this invention, the energy efficiency of distillation is excellent, and energy saving can be achieved. Furthermore, ethanol difficult to remove heretofore can be efficiently removed, and highly pure methanol having a very small ethanol content can be obtained continuously and stably. The process, therefore, is very advantageous industrially.

The following examples illustrate the present invention further.

BRIEF DESCRIPTION OF THE DRAWING(S)

Figure 2:
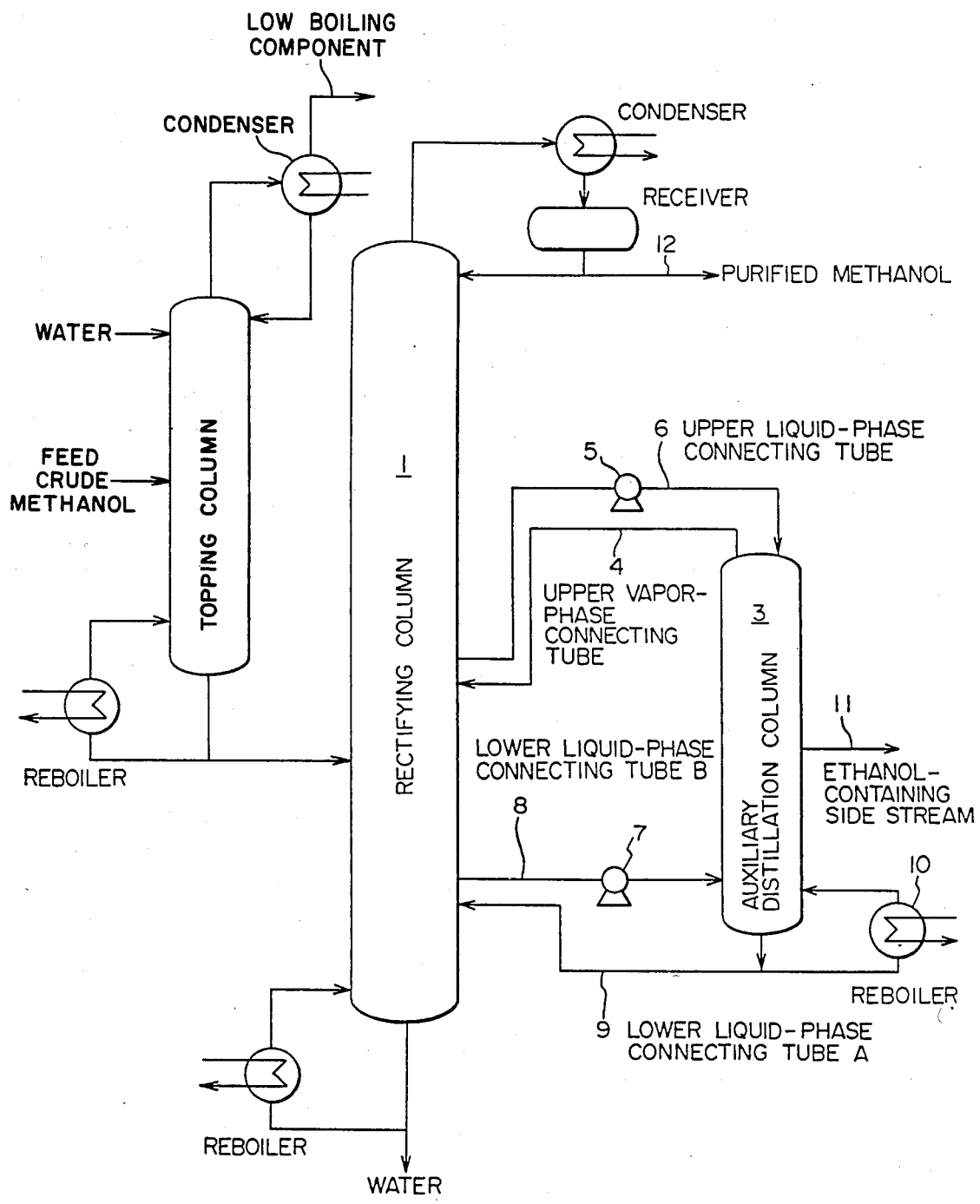

FIG. 1 is a flow diagram in the case where the crude synthetic methanol is directly introduced to the distillation system of the invention, and FIG. 2 is a flow diagram illustrating the case where the crude synthetic methanol is first treated at a topping column, and then fed to the distillation system. In FIG. 2, there are two possible cases, the first where water is added and the second where water is not added into the top of the topping column.

EXAMPLE 1

Crude methanol obtained by reacting carbon monoxide with hydrogen at 280° C. and 100 atmospheres in the presence of a copper-zinc type catalyst was distilled under atmospheric pressure in a topping column to remove dissolved gases and low-boiling impurities. Then, referring to FIG. 1, crude methanol was fed to a middle plate (58th plate from the top) of a rectifying column 1 from a material feed tube 2 at a rate of 25.15 tons/hour. Side by side with the rectifying column, an auxiliary distillation column 3 having 30 plates was provided, and a vapor-phase portion on a top plate of the auxiliary distillation column was connected to a vapor-phase portion on the 53rd plate of the rectifying column from the top by a tube 4. The vapor was recycled to the rectifying column at a rate of 18.41 tons/hour. A liquid-phase portion at the 53rd plate of the rectifying column from the top was connected to a liquid-phase portion at the top of the auxiliary distillation column by a tube 6 via a pump 5. The liquid component was conducted to the auxiliary distillation column at a rate of 18.13 tons/hour. Furthermore, a liquid-phase portion on the 67th plate of the rectifying column from the top was connected to a liquid phase portion at the bottom of the auxiliary distillation column by a tube 8 via a pump 7. The liquid component was conducted to the auxiliary distillation column at a rate of 10.93 tons/hour. A liquid-phase portion at the 70th plate of the rectifying column from the top was connected to a liquid-phase portion at a bottom plate of the auxiliary distillation column by a tube 9, and the liquid was returned to the rectifying column at a rate of 10.49 tons/hour. A reboiler 10 was provided at the bottom of the auxiliary distillation column, and the amount of the vapor returned from a tube 4 was controlled by the reboiler. A side stream containing 7.8% of ethanol was withdrawn from the 20th plate of the auxiliary bottom column from above via a tube 11 at a rate of 160 kg/hour. The reflux ratio at the top of the rectifying column was 2, and the concentration of ethanol contained in purified methanol 12 obtained from the top of the rectifying column at a rate of 18.75 tons/hour was 5.2 ppm (by weight). The amount of methanol lost as the side stream was only 0.5% of the methanol fed.

The composition of the feed, the rectifying conditions, and the results of the distillation are summarized in Tables 1 and 2.

EXAMPLE 2

Example 1 was repeated except that the amount of the crude methanol fed from the tube 2 in FIG. 1 was changed to 33.52 tons/hour; the amount of the vapor returned from the tube 4, to 15.06 tons/hour; the amount of the liquid component introduced from the tube 6, to 14.55 tons/hour; the amount of the liquid component introduced from the tube 8, to 9.48 tons/hour; the amount of the liquid component returned from the tube 9, to 8.75 tons/hour; and the amount of the side stream withdrawn from the tube 11, to 220 kg/hour. Purified methanol containing 9 ppm of ethanol was withdrawn from the tube 12 at a rate of 18.75 tons/hour and simultaneously, low-grade methanol containing 0.13% of ethanol was withdrawn from the 37th plate of the rectifier via the tube 13 at a rate of 6.24 tons/hour. At this time, the amount of ethanol lost as a result of being withdrawn as the side stream from the auxiliary distillation column was 0.6%. This corresponds to an overall reflux ratio of 1.3, and to an increase of 30% in the amount of production. The results are shown in Table 2.

COMPARATIVE EXAMPLE

Example 1 was repeated except that the auxiliary distillation column was not used. The starting material was fed to the 60th plate of the rectifying column from the top at a rate of 25.15 tons/hour. A side stream was withdrawn from the 65th plate at a rate of 160 kg/hour.

The reflux ratio was adjusted to 2. At this time, methanol was obtained as the overhead product at a rate of 18.75 tons/hour. Its ethanol content was 104 ppm, and the concentration of the bottom product was 77 ppm. The results are shown in Table 2.

TABLE 1

| Feed composition | | |
|---|---|---|
| Methanol: 74.9% by weight | | |
| Water: 25.0% by weight | | |
| Ethanol: 0.05% by weight | | |
| Higher alcohol: 0.05% by weight | | |
| Column size | Diameter | Height |
| Rectifying column | 3.6 m | 28 m |
| Auxiliary column | 2.0 m | 12 m |
| Reboiler heating temperature (for both columns) | | |
| 130° C. (using 3 kg/cm$^2$ steam) | | |

TABLE 2

| | Example 1 | Example 2 | Comparative Example |
|---|---|---|---|
| Amount of the feed (tons/hr) | 25.15 | 33.52 | 25.15 |
| Products | | | |
| Highly purified methanol (ethanol content) | 18.75 tons/hr (5.2 wt. ppm) | 18.75 tons/hr (9 wt. ppm) | — |
| Low-grade product | — | 6.24 tons/hr | 18.75 tons/hr (containing 104 ppm of ethanol) |
| Reflux ratio | 2.0 | 1.3(*) | 2.0 |
| Energy required per ton of the product (MM Kcal/ton) | 0.79 | 0.60 | 0.79 |
| Loss of methanol (%) | 0.5 | 0.6 | 0.5 |

(*) total reflux ratio including the low-grade product

What is claimed is:

1. A process for purifying methanol which comprises;
   (a) introducing crude synthetic methanol obtained by catalytic reaction of carbon oxide and hydrogen into a rectifying column,
   (b) forcibly conducting liquid components at a liquid-phase portion on a plate located between the bottom plate and the material feed plate of the rectifying column to a liquid-phase portion on a plate near the bottom of an auxiliary distillation column which is provided side-by-side with the rectifying column through a lower liquid-phase connecting tube B,
   (c) conducting liquid components at a liquid-phase portion on a plate at the bottom of the auxiliary distillation column to the liquid-phase portion on the plate located between the bottom plate and the material feed plate of the rectifying column through a lower liquid-phase connecting tube A,
   (d) evaporating the bottom components in the auxiliary distillation column by heating a reboiler provided at the bottom portion of the auxiliary distillation column,
   (e) forcibly conducting liquid components at a liquid-phase portion on a plate slightly above the material feed plate of the rectifying column to a liquid-phase portion on a plate at the top of the auxiliary distillation column through an upper liquid-phase connecting tube,
   (f) conducting vapor components at a vapor-phase portion on a plate at the top of the auxiliary distillation column to the vapor-phase portion on a plate slightly above a material feed plate on the rectifying column through an upper vapor-phase connecting tube,
   (g) thereby carrying out the distillation while circulating the vapor components and the liquid components between the rectifying column and the auxiliary distillation column
   (h) withdrawing product methanol from the top of the rectifying column and the remaining water from the bottom of the column, and
   (i) withdrawing a side stream rich in ethanol from the liquid-phase portion of a plate located in the middle part of the auxiliary distillation column.

2. The process of claim 1 wherein the crude synthetic methanol is introduced into the rectifying column after it is first introduced into a topping column and distilled to remove low-boiling components from the topping column.

3. The process of claim 2 wherein the crude synthetic methanol is distilled with the addition of water in the topping column.

4. The process of claim 1 wherein the auxiliary distillation column has as many as 1/5 to 4/5 plates of the plates of the rectifying column.

5. The process of claim 1 wherein the auxiliary distillation column has about 10 to 40 theoretical plates.

6. The proces of claim 1 wherein the upper vapor-phase connecting tube is connected to a vapor-phase portion on a plate positioned within 9/20 to 17/20 of the number of the plates of the rectifying column counted from its top.

7. The process of claim 1 wherein the lower liquid-phase connecting tube A is connected to a liquid-phase portion on a plate positioned within 1/40 to 3/20 of the number of the plates of the rectifying column counted from its bottom.

8. The process of claim 1 wherein the lower liquid-phase connecting tube B is connected to a liquid-phase portion on a plate positioned within the range of 1/40 to 3/20 of the number of the plates of the rectifying column counted from its bottom.

9. The process of claim 1 wherein the rectifying column is operated at a reflux ration in the range of 0.8 to 3.

* * * * *